(12) United States Patent
Choi et al.

(10) Patent No.: US 7,718,840 B2
(45) Date of Patent: May 18, 2010

(54) PROCESS FOR PRODUCTION OF LIGHT OLEFINS FROM HYDROCARBON FEEDSTOCK

(75) Inventors: Sun Choi, Daejeon (KR); Yong Seung Kim, Daejeon (KR); Deuk Soo Park, Gyeonggi-do (KR); Suk Joon Kim, Daejeon (KR); Il Mo Yang, Seoul (KR); Hee Young Kim, Daejeon (KR); Yong Ki Park, Daejeon (KR); Chul Wee Lee, Daejeon (KR); Won Choon Choi, Daejeon (KR); Kwang An Ko, Gwangju (KR); Na Young Kang, Chungcheongnam-do (KR)

(73) Assignees: SK Energy Co., Ltd. (KR); Korea Research Institute of Chemical Technology (KR)

( * ) Notice: Subject to any disclaimer, the term of this patent is extended or adjusted under 35 U.S.C. 154(b) by 405 days.

(21) Appl. No.: 11/426,847

(22) Filed: Jun. 27, 2006

(65) Prior Publication Data
US 2007/0010699 A1    Jan. 11, 2007

(30) Foreign Application Priority Data
Oct. 7, 2005   (KR) .................. 10-2005-0094468
Jun. 13, 2006  (KR) .................. 10-2006-0053069

(51) Int. Cl.
*C07C 4/02* (2006.01)
*C10G 11/02* (2006.01)
*B01J 29/06* (2006.01)
*B01J 27/182* (2006.01)

(52) U.S. Cl. .............. 585/651; 585/652; 585/653; 208/114; 208/120.01; 208/120.25; 208/120.1; 208/120.2; 208/121; 208/122; 208/124; 502/60; 502/77; 502/78; 502/79; 502/208; 502/214

(58) Field of Classification Search .............. 585/650, 585/651, 653; 208/114, 121, 120.01, 120.25, 208/120.1, 120.2, 122, 124; 502/77–79, 502/208, 214, 60
See application file for complete search history.

(56) References Cited

U.S. PATENT DOCUMENTS

| 6,835,883 | B2 | 12/2004 | Chester et al. |
| 6,867,341 | B1 | 3/2005 | Abrevaya et al. |
| 2005/0020867 | A1 * | 1/2005 | Xie et al. .................. 585/651 |

FOREIGN PATENT DOCUMENTS

| JP | 06-192135 A | 7/1994 |
| JP | 06-199707 A | 7/1994 |

* cited by examiner

*Primary Examiner*—In Suk Bullock (57) ABSTRACT

Disclosed is a process for producing light olefins from hydrocarbon feedstock. The process is characterized in that a porous molecular sieve catalyst consisting of a product obtained by evaporating water from a raw material mixture comprising a molecular sieve with a framework of Si—OH—Al— groups, a water-insoluble metal salt, and a phosphate compound, is used to produce light olefins, particularly ethylene and propylene, from hydrocarbon, while maintaining excellent selectivity to light olefins. According to the process, by the use of a specific catalyst with hydrothermal stability, light olefins can be selectively produced in high yield with high selectivity from hydrocarbon feedstock, particularly full-range naphtha. In particular, the process can maintain higher cracking activity than the reaction temperature required in the prior thermal cracking process for the production of light olefins, and thus, can produce light olefins with high selectivity and conversion from hydrocarbon feedstock.

7 Claims, 1 Drawing Sheet

FIG. 1

PROCESS FOR PRODUCTION OF LIGHT OLEFINS FROM HYDROCARBON FEEDSTOCK

BACKGROUND OF THE INVENTION

1. Field of the Invention

The present invention relates to a process for producing light olefins from hydrocarbon feedstock, and more particularly to a process for producing light olefins at high yield with high selectivity from hydrocarbon feedstock using a catalyst which, even in an atmosphere of high temperature and humidity, has a relatively stable structure, thereby maintaining its catalytic activity over a long period of time, and shows hydrothermal stability.

2. Description of the Related Art

Olefins, particularly light olefins, such as ethylene and propylene, are widely used in the petroleum chemical industry.

These light olefins are generally produced by the thermal cracking (steam cracking) of naphtha in the presence of steam. The steam cracking technology is being improved in many fields in order to cope with high process temperature and a reduction in residence time and to optimize energy efficiency. However, it is not easy to improve energy efficiency merely by simple improvements in engineering technology, and the steam cracking process currently accounts for about 40% of the total energy required in the petroleum chemical industry. Accordingly, to reduce environmental pollution and increase economic efficiency, there is a need for improved process technologies for the optimization of energy, the reduction of feedstock use, the minimization of carbon dioxide discharge, etc. Also, light naphtha is typically used as feedstock, but is expensive compared to full-range naphtha as described later, and thus, will necessarily act as a limitation in increasing economic efficiency. Particularly, in the steam cracking technology, that is currently applied, not only it is not easy to control the composition of olefins but also the reaction temperature is a level of 800-900° C., indicating a requirement for a large amount of thermal energy. Thus, a need for improvement in steam cracking technology has suggested.

Also, light olefin compounds can be produced by a fluid catalytic cracking (FCC) process. This FCC process is widely known in the art as catalytic cracking technology using a catalyst having the form of fine particles, which behaves like fluid when treated with steam. Particularly, deep catalytic cracking (DCC) technology is known which is a process developed by modifying the FCC process in order to increase the yield of olefins (mainly, propylene) other than gasoline. In the FCC process, a heavier fraction than full-range naphtha used in the present invention, such as vacuum residue, atmospheric residue, or gaseous oil, is used as feedstock.

Regarding the production of olefins, in addition to the above-described steam cracking and FCC processes, olefin conversion processes using catalytic cracking have been proposed. In most of these processes, the HZSM-5 catalyst as a solid acid catalyst is widely used. However, in the conventional catalytic cracking processes using the solid acid catalyst, the reaction temperature is typically at least 650° C., and at least 30% of the reaction feed is steam. The porous solid acid catalyst (e.g., zeolite) used in these catalytic cracking processes has problems in that, when it is placed in a steam atmosphere of more than 500° C., the dealumination of its tetrahedral framework will occur to cause structural breakdown thereof and at the same time, the acid sites of the solid acid catalyst will be reduced, resulting in a rapid reduction in catalytic activity and reactivity.

Accordingly, in the above-described conventional light olefin production processes including the catalytic cracking process, studies are actively performed to decrease the instability of the catalyst, and thus, a reduction in process performance, which occur when the catalyst is placed in a severe process atmosphere of high temperature and humidity.

Regarding these studies, U.S. Pat. No. 6,867,341 discloses a naphtha cracking catalyst obtained by controlling the distribution of aluminum atoms and crystal size of zeolite, as well as a process for cracking naphtha using this catalyst. According to the disclosure of said patent, the catalyst is designed so that the production of aromatic compounds on the pore surface can be minimized by chemically neutralizing aluminum present outside the pores, whereas ethylene and propylene, having small sizes, can be more selectively produced by increasing the concentration of aluminum ions inside the pores to increase the number of acid sites. Meanwhile, as disclosed in said patent, when a ferrierite zeolite catalyst obtained by this technology is used in catalytic cracking, the reactivity of the catalyst will become excellent even in a relatively severe process environment, such as maintaining the catalyst in an atmosphere of 50% steam at 690° C. for 2 hours. Regarding the hydrothermal stability of the catalyst, however, it is expected that the structural stability and reactivity of the catalyst cannot be secured when it is treated with 100% steam at 750° C. for 24 hours.

U.S. Pat. No. 6,835,863 discloses a process for producing light olefins by catalytically cracking naphtha (boiling point: 27-221° C.) using a pelletized catalyst containing 5-75% by weight of ZSM-5 and/or ZSM-11, 25-95% by weight of silica or kaolin and 0.5-10% by weight of phosphorus. However, there is no mention of hydrothermal stability in a severe environment of high temperature and humidity.

Japanese patent laid-open publication No. Hei 6-192135 discloses a catalytic cracking process for producing ethylene and propylene from $C_{2-12}$ paraffin-containing light naphtha (density: 0.683 g/cc; composition: 42.7 wt % n-paraffin, 36.1 wt % iso-paraffin, 0.1 wt % olefins, 14.0 wt % naphthene, and 7.1 wt % aromatics; and the distribution of the paraffin component: 0.1 wt % $C_3$, 5.2 wt % $C_4$, 18.7 wt % $C_5$, 19.0 wt % $C_6$, 15.2 wt % $C_7$, 13.5 wt % $C_8$, 6.1 wt % $C_9$, 0.1 wt % $C_{10}$ and 0.1 wt % $C_{11}$) using HZSM-5 and HZSM-11 catalysts (molar ratio of $SiO_2/Al_2O_3$: 150-300) at a temperature of 620-750° C. and a WHSV of 1-200 $h^{-1}$. According to the disclosure of said patent, under reaction conditions of 680° C. and a WHSV of 25 $h^{-1}$, a conversion rate of 93.6 wt % and ethylene+propylene production of 44.9 wt % are shown. However, the HZSM-5 or HZSM-11 catalyst is used in the catalytic cracking reaction in an unpelletized state, and steam or inert gas is not fed during the reaction. Thus, the catalyst has excellent initial activity, but there is a possibility for the catalyst to be easily inactivated. For this reason, it is expected that the reactivity of the catalyst in a severe environment of high temperature and humidity will be remarkably reduced.

Meanwhile, Japanese patent laid-open publication No. 6-199707 reports that, in a catalytic cracking process for producing ethylene and propylene as main products from light naphtha containing $C_{2-12}$ paraffin, the use of a proton-zeolite ($SiO_2/Al_2O_3$=20-500) catalyst loaded with 100 ppm iron (Fe) allows light olefins to be produced with good selectivity. The catalyst has excellent initial activity since steam or inert gas is not fed during the reaction, but there is a possibility for the catalyst to be easily deactivated in a high-temperature reaction involving steam. For this reason, it is expected that the reactivity of the catalyst in a severe environment of high temperature and humidity will be remarkably reduced.

Accordingly, there is an urgent need for the development of a process where reaction activity is maintained even in a severe process environment of high temperature and humidity so that light olefins, such as ethylene and propylene, can be selectively produced with high conversion and selectivity from reaction feedstock, particularly full-range naphtha.

SUMMARY OF THE INVENTION

Accordingly, the present inventors have conducted extensive studies to solve the above problems occurring in the prior art and as a result, found that when a specific catalyst with excellent hydrothermal stability was used, light olefins could be produced at high yield with high selectivity from hydrocarbon feedstock without a reduction in the reactivity of the catalyst even in a severe process environment. On the basis of this fact, the present invention has been completed.

Therefore, it is an object of the present invention to provide a process capable of selectively producing light olefins, such as ethylene and propylene, in high yield with high selectivity from hydrocarbon feedstock, particularly full-range naphtha, even in a severe environment of high temperature and humidity.

Another object of the present invention is to provide a process where high cracking activity is maintained even at a temperature lower than the reaction temperature required in the prior thermal cracking process for the production of light olefins, so that light olefins can be produced with high selectivity and conversion from hydrocarbon feedstock.

To achieve the above objects, the present invention provides a process for producing light olefins from hydrocarbon feedstock, comprising the steps of: (a) providing a hydrocarbon fraction as feedstock; (b) feeding the feedstock into at least one fixed-bed or fluidized-bed reactor where it is allowed to react in the presence of a catalyst; and (c) separating and recovering light olefins from the effluent of the reaction zone; in which the catalyst consists of a product obtained by the water evaporation of a raw material mixture comprising 100 parts by weight of a molecule sieve with a framework of —Si—OH—Al— groups, 0.01-5.0 parts by weight of a water-insoluble metal salt, and 0.05-17.0 parts by weight of a phosphate compound.

In the inventive process, the feedstock is preferably full-range naphtha or kerosene, and more preferably naphtha containing $C_{2-15}$ hydrocarbons.

Preferably, the total content of paraffin components (n-paraffin and iso-paraffin) in the full-range naphtha is 60-90% by weight, and the content of olefins in the naphtha is less than 20% by weight.

Also, the inventive process may further comprise the steps of mixing $C_{4-5}$ hydrocarbons remaining after the separation and recovery of light olefins in the step (c) with naphtha and providing the $C_{4-5}$ hydrocarbon/naphtha mixture as feedstock.

Meanwhile, if the reactor is a fixed-bed reactor, the reaction will preferably be carried out at a temperature of 500-750° C., a hydrocarbon/steam weight ratio of 0.01-10, and a space velocity of 0.1-20 $h^{-1}$.

If the reactor is a fluidized-bed reactor, the reaction will preferably be carried out at a temperature of 500-750° C., a hydrocarbon/steam weight ratio of 0.01-10, a catalyst/hydrocarbon weight ratio of 1-50, and a hydrocarbon residence time of 0.1-600 seconds.

Meanwhile, if the catalyst is used after steam treatment in an atmosphere of 100% steam at 750° C. for 24 hours, the total content of ethylene and propylene in the effluent of the reaction zone will be more than 30% by weight, and the ethylene/propylene weight ratio will be 0.25-1.5.

BRIEF DESCRIPTION OF THE DRAWING

The above and other objects, features and advantages of the present invention will be more clearly understood from the following detailed description taken in conjunction with the accompanying drawing, in which.

DESCRIPTION OF THE PREFERRED EMBODIMENTS

Hereinafter, the present invention will be described in more detail.

As described above, according to the present invention, the use of the porous molecular sieve catalyst with hydrothermal stability allows light olefins to be selectively produced at high yield with high selectivity from hydrocarbon feedstock, particularly full-range naphtha.

The porous molecular sieve catalyst used in the inventive process for the production of light olefins consists of a product obtained by the water evaporation of a raw material mixture comprising 100 parts by weight of a molecule sieve with a framework of —Si—OH—Al— groups, 0.01-5.0 parts by weight of a water-insoluble metal salt, and 0.05-17.0 parts by weight of a phosphate compound. When this product is used as a catalyst for the production of light olefins, it can show excellent hydrothermal stability, reaction activity and selectivity while increasing economic efficiency. The porous molecular sieve catalyst can be prepared to have the desired physical and chemical properties by suitably selecting and adjusting the kind of starting material for a modifier, the composition ratio of each component, the loading amount, the pH and temperature of the solution during loading, etc. During the catalyst preparation process, the following technical particulars are considered:

(1) technology of selectively modifying only the surface pores of a molecular sieve with a phosphate compound which is present in the form of an ion selected from a monohydrogen phosphate ion, a dihydrogen phosphate ion, and a phosphate ion;

(2) technology of using a water-insoluble metal salt to prevent the ion exchange of protons in the molecular sieve with a large amount of dissolved metal ions and at the same time, to stabilize a phosphate compound of modifying the molecular sieve; and (3) technology of stabilizing a molecular sieve modified with a phosphate compound and a metal by water evaporation.

With this technical background, any support for the catalyst may be used if it is a molecular sieve containing a framework of —Si—OH—Al— groups.

It is preferable to use any one selected from mesoporous molecular sieves with a pore size of 10-100 Å and an Si/Al molar ratio of 1-300 and preferably about 25-80, including zeolites with a pore size of 4-10 Å.

Among them, more preferred are ZSM-5, Ferrierite, ZSM-11, Mordenite, Beta-zeolite, MCM-22, L-zeolite, MCM-41, SBA-15 and/or Y-zeolite, the general properties of which are already widely known in the art.

As used herein, the term water-insoluble metal salt means a metal salt with a solubility product (Ksp) of less than $10^{-4}$, i.e., a pKsp of more than 4. An example of this metal salt may be an oxide, hydroxide, carbonate or oxalate of a metal with an oxidation state of more than +2. Preferably, the metal salt is an oxide, hydroxide, carbonate or oxalate of at least one metal selected from the group consisting of alkaline earth metals, transition metals and heavy metals with an oxidation state of +3 to +5.

Preferably, the alkaline earth metals may include Mg, Ca, Sr and Ba, the transition metals may include Ti, V, Cr, Mn, Fe, Co, Ni and Cu, and the heavy metals may include B, Al, Ga, In, Ti, Sn, Pb, Sb and Bi.

Meanwhile, the phosphate compound is not specifically limited if it is one known in the art. However, because the use of phosphoric acid as the phosphate compound has a disadvantage in that the crystallinity of a porous material is reduced, alkyl phosphine derivatives in place of phosphoric acid may also be used but have a problem in that they are not suitable for use in mass production because they are uneconomical and not easy to handle. For this reason, it is preferable to use phosphoric acid, ammonium phosphate [$(NH_4)_3PO_4$, $(NH_4)_2HPO_4$, $(NH_4)H_2PO_4$], or alkyl phosphate as the phosphate compound.

It is generally known that the acid dissociation constants pKa(1), pKa(2) and pKa(3) of phosphoric acid ($H_3PO_4$) are 2.2, 7.2 and 12.3, respectively, and the phosphoric acid is present as a monohydrogen phosphate ion ([$HPO_4$]$^{2-}$), a dihydrogen phosphate ion ([$H_2PO_4$]$^-$) and a phosphate ion ([$PO_4$]$^{3-}$) at pHs 2.2, 7.2 and 12.3, respectively. Thus, it will be obvious that the desired chemical species of phosphate ions can be selectively formed by suitably adjusting the pH of an aqueous solution containing the phosphate compound.

The porous molecular sieve catalyst formed from the above-described composition is modified with one compound selected from compounds represented by the following formulas 1 to 3:

[Formula 1]

$M_x(H_2PO_4)_y$, wherein M is a metal, x is 1, and y is an integer from 2 to 6;

[Formula 2]

$M_x(HPO_4)_y$, wherein M is a metal, x is 2, and y is an integer of from 2 to 6;

and

[Formula 3]

$M_x(PO_4)_y$, wherein M is a metal, x is 3, and y is an integer from 2 to 6.

Accordingly, exposed acid sites outside the pores of the porous molecular sieve are selectively modified with a modifier having physical and chemical stabilities in an atmosphere of high temperature and humidity, so that the surface of zeolite can be protected from dealumination.

Although the description for the preparation of the molecular sieve catalyst is not restricted to a certain theory, it is believed that the —Si—OH—Al— groups forming the molecular sieve are modified with the phosphate compound/metal composite structure as shown in the following reaction schemes 1 and 2 so as to be condensed with the proton of zeolite so that a =P=O group stabilizes unstable Al while two —OH groups are stabilized with the metal, whereby the framework structure is relatively stably maintained even in an atmosphere of high temperature and humidity:

A method for preparing the porous molecular sieve catalyst can be broadly divided into two methods and involve the step of removing water contained in the above-described raw material mixture by a selective evaporation process so as to recover a solid product.

Hereinafter, the preparation method of the catalyst according to one preferred embodiment of the present invention will be described.

(1) The phosphate compound is added to and mixed with an aqueous slurry containing the water-insoluble metal salt. The mixture is adjusted to a suitable pH using a conventional alkaline or acidic aqueous solution, such as NaOH, KOH, $NH_4OH$, HCl or $HNO_3$, and stirred at a temperature of about 20-60° C., and preferably about 40-50° C., for about 30 minutes to 3 hours, and preferably about 1-3 hours, so that the phosphate compound is present in the form of an ion selected from a monohydrogen phosphate ion, a dihydrogen phosphate ion and a phosphate ion, in the aqueous solution.

Particularly, it is preferable that the mixture is adjusted to a desired pH range so that only one chemical species of phosphate ion that exists at this pH range will be formed in the aqueous solution. Namely, if a specific pH range is not met, one or more species of phosphate ions will coexist in the aqueous solution so that a chemical species of modifying the pore surface of the molecular sieve will not be uniform, thus making it difficult to secure the durability of the modified catalyst.

(2) To the mixture of the part (1), a molecular sieve with a framework of —Si—OH—Al— groups is added. The resulting mixture is stirred at a temperature of preferably about 10-90° C., and more preferably about 50-70° C., in a specific pH range corresponding to purpose, until water in the aqueous slurry is completely evaporated. Thus, the phosphate ion species modifying the molecular sieve is stabilized with metal ions while water present in the slurry is removed. Then, vacuum filtration is performed to recover the solid product. In this way, the molecular sieve catalyst having the —Si—OH—Al— framework modified with the phosphate-metal salt is prepared.

Meanwhile, the composition of the raw material mixture used in the preparation of the catalyst is as follows: 100 parts by weight of the molecular sieve having the —Si—OH—

Al— framework; 0.01-5.0 parts by weight of the water-insoluble metal salt; and 0.05-17.0 parts by weight of the phosphate compound.

The preparation method of the catalyst according to another embodiment of the present invention will now be described.

(1) A phosphate compound is added to and mixed with an aqueous slurry containing the water-insoluble metal salt. The mixture is adjusted to a suitable pH using a conventional alkaline or acidic aqueous solution, such as NaOH, KOH, $NH_4OH$, HCl or $HNO_3$, and stirred at a temperature of about 20-60° C., and preferably about 40-50° C., for about 30 minutes to 3 hours, and preferably about 1-3 hours, so that the phosphate compound exists in the form of an ion selected from a monohydrogen phosphate ion, a dihydrogen phosphate ion and a phosphate ion, in the aqueous slurry. Then, the aqueous slurry is subjected to water evaporation at a temperature of preferably 10-90° C., and more preferably 50-70° C., in a specific pH range suitable for the purpose, until water in the aqueous slurry completely evaporates. Then, the solid product is vacuum filtered and washed to separate a first solid product. In this way, the water-insoluble phosphate-metal salt is prepared.

(2) The first solid product of the part (1) is added to and mixed with an aqueous solution containing a molecular sieve with a framework of —Si—OH—Al— groups. The resulting mixture is stirred at a temperature of preferably about 20-60° C., and more preferably about 40-50° C., for about 30 minutes to 7 hours, and preferably about 1-5 hours, until water in the mixture completely evaporates. Then, the remaining solid product is vacuum filtered to separate a second solid product. In this way, the molecular sieve catalyst having the —Si—OH—Al— framework modified with the phosphate-metal salt is prepared.

Meanwhile, the raw material mixture used in the preparation of the catalyst is used in such a controlled manner that the composition of the raw material mixture is as follows: 100 parts by weight of the molecular sieve having the —Si—OH—Al— framework; 0.01-5.0 parts by weight of the water-insoluble metal salt; and 0.05-17.0 parts by weight of the phosphate compound. Particularly, it is preferable in terms of the desired effect that the first solid product should be used in an amount of 0.01-20.0 parts by weight based on 100 parts by weight of the molecular sieve.

In the above-described methods of preparing the catalyst, it is necessary to find conditions where the metal ions formed by the dissolution of some of the metal salt in the aqueous solution can stabilize only the modified phosphate ion species without ion exchange with the proton of the molecular sieve. Otherwise the dissolved metal ions will be ion-exchanged with the proton of the molecular sieve to reduce the number of acid sites, resulting in a reduction in reactivity of modified catalysts.

Accordingly, as described above, by the use of a water-insoluble metal salt having a solubility product of less than $10^{-4}$ in aqueous solution, and preferably, an oxide, hydroxide, carbonate or oxalate of at least one metal selected from the group consisting of alkaline earth metals, transition metals, and heavy metals with an oxidation state of +3 to +5, it is possible to substantially prevent the phenomenon of ion exchange with the proton of the molecular sieve by the presence of a large amount of metal ions, which is a problem in the case of using water-soluble metal salts, and at the same time, it is possible to maximize the effect of stabilizing the modified phosphate ions with the desired metal ions.

Meanwhile, the raw material mixture in the aqueous slurry for the preparation of the catalyst must be maintained at the following composition: 100 parts by weight of the molecular sieve; 0.01-5.0 parts by weight of the water-insoluble metal salt; and 0.05-17.0 parts by weight of the phosphate compound. If the composition of the raw material mixture is out of the specified composition range, the surface pores of the molecular sieve will not be selectively modified with the modifier, and the number of acid sites will be rather reduced, leading to a reduction in catalytic activity. Particularly, the molar ratio of the water-insoluble metal salt to the phosphate compound is 1.0:0.3-10.0, and preferably 1.0:0.7-5.0. If the molar ratio of the phosphate compound to the water-insoluble metal salt is less than 0.3, there will be a problem in that unnecessary metal ions are present in excess so that the number of acid sites in the molecular sieve is reduced, leading to a reduction in the reactivity of the modified catalyst. On the other hand, if the ratio of the phosphate compound to the water-insoluble metal salt is less more than 10.0, there will be a problem in that the molecular sieve framework is not sufficiently modified so that the hydrothermal stability of the modified molecular sieve becomes poor.

Hereinafter, the inventive process for producing light olefins from hydrocarbon feedstock using the above-described porous molecular sieve catalyst, where the hydrothermal stability of the catalyst in a sever environment of high temperature and humidity is necessarily required, will be described.

As the hydrocarbon feedstock, full-range naphtha or kerosene may be used. More preferably, full-range naphtha having $C_{2-15}$ hydrocarbons may be used. The most suitable process reaction for this hydrocarbon feedstock may be catalytic cracking reaction but is not specifically limited thereto.

Examples of the feedstock which can be used in the present invention include, in addition to full-range naphtha, expensive light naphtha used in a steam cracking process for the production of light olefins, and olefin-containing feedstock typically used in a plurality of catalytic cracking processes, and $C_{20-30}$ heavy fractions which have been used in the prior FCC process.

Among them, the full-range naphtha is a fraction containing $C_{2-12}$ hydrocarbons produced directly in crude oil refining processes and contains paraffins (n-paraffin and iso-paraffin), naphthene, aromatic compounds, etc., and may sometimes contain olefin compounds. Generally, the higher the content of paraffin components in naphtha, the slighter naphtha becomes, and on the other hand, the lower the content of paraffin components, the heavier naphtha becomes.

According to the present invention, the feedstock is selected by considering yield, economic efficiency, etc. Under this consideration, full-range naphtha may be used where the total content of paraffin components (n-paraffin and iso-paraffin) is 60-90 wt %, more preferably 60-80 wt %, and most preferably 60-70 wt %. Also, the selected naphtha may contain olefins in an amount of less than 20 wt %, preferably less than 10 wt %, and most preferably less than 5 wt %. Table 1 below shows an illustrative feedstock composition (unit: wt %) which can be used in the present invention.

Moreover, in the present invention, the naphtha feedstock may also be used in a mixture with $C_{4-5}$ hydrocarbons remaining after the separation and recovery of light olefins and heavy products from the effluent of a reaction zone containing the catalyst.

TABLE 1

|  | n-paraffin | iso-paraffin | naphthene | aromatics | olefins |
|---|---|---|---|---|---|
| Naphtha | 31.7% | 53.0% | 9.3% | 2.7% | 3.3% |

In the present invention, the reaction zone may comprise at least one reactor, and preferably a fixed-bed or fluidized-bed reactor. In the reactor, the feedstock is converted to a large amount of light olefins by a conversion reaction (e.g., a catalytic cracking reaction) with the inventive catalyst.

Generally, catalytic activity greatly depends on reaction temperature, space velocity, the naphtha/steam weight ratio, etc. In this case, reaction conditions determined with the following considerations must be presented: the lowest possible temperature to minimize energy consumption, the optimal conversion, the optimal olefin production, the minimization of catalyst deactivation caused by coke production, etc. According to a preferred embodiment of the present invention, the reaction temperature is about 500-750° C., preferably about 600-700° C., and more preferably about 610-680° C. Also, the hydrocarbon/steam weight ratio is about 0.01-10, preferably about 0.1-2.0, and more preferably about 0.3-1.0.

If the fixed-bed reactor is used, the space velocity will be about 0.1-20 $h^1$, preferably about 0.3-10 $h^{-1}$, and more preferably about 0.5-4 $h^{-1}$. Furthermore, if the fluidized-bed reactor is used, the catalyst/hydrocarbon weight ratio will be about 1-50, preferably about 5-30, and more preferably about 10-20, and the residence time of hydrocarbons will be about 0.1-600 seconds, preferably about 0.5-120 seconds, and more preferably about 1-20 seconds.

Meanwhile, in order to examine if the molecular sieve catalyst according to the present invention can maintain its catalytic activity to some extent even in a severe environment or is deactivated in this environment, the inventive catalyst was steamed in an atmosphere of 100% steam at 750° C. for 24 hours. Namely, if the inventive catalyst is used after steaming in the above-described atmosphere, the content of light olefins (i.e., ethylene and propylene) in the effluent of said reaction zone will preferably be more than about 30 wt %, more preferably more than about 35 wt %, and most preferably more than about 40 wt %. In this case, the ethylene/propylene weight ratio is preferably about 0.25-1.5, more preferably 0.5-1.4, and most preferably 0.7-1.3, indicating that propylene is produced in a relatively large amount.

Hereinafter, the present invention will be described in more detail by examples. It is to be understood, however, that these examples are not construed to limit the scope of the present invention.

EXAMPLE 1

A) Preparation of Catalyst

To 100 mL of distilled water, 10 g of HZSM-5 (Zeolyst) with a Si/Al molar ratio of 25, and 0.55 g of concentrated phosphoric acid (85% $H_3PO_4$), were added and stirred for 20 minutes. To the stirred solution, 0.36 g of $Mg(OH)_2$ was added and the mixture was adjusted to a pH of 7-8 using ammonia water, followed by stirring at a temperature of about 45° C. for about 20 minutes. Next, the mixture was stirred at about 50° C. until the water completely evaporated, and then, vacuum filtration was used to separate the solid product. The separated solid product was calcined in air at a temperature of 500° C. for 5 hours, thus preparing an Mg—$HPO_4$—HZSM-5 catalyst.

B) Steaming Step for Evaluation of Hydrothermal Stability

To evaluate the hydrothermal stability of the catalyst, the catalyst was maintained in an atmosphere of 100% steam at 750° C. for 24 hours.

C) Production of Light Olefins

Figure 1:
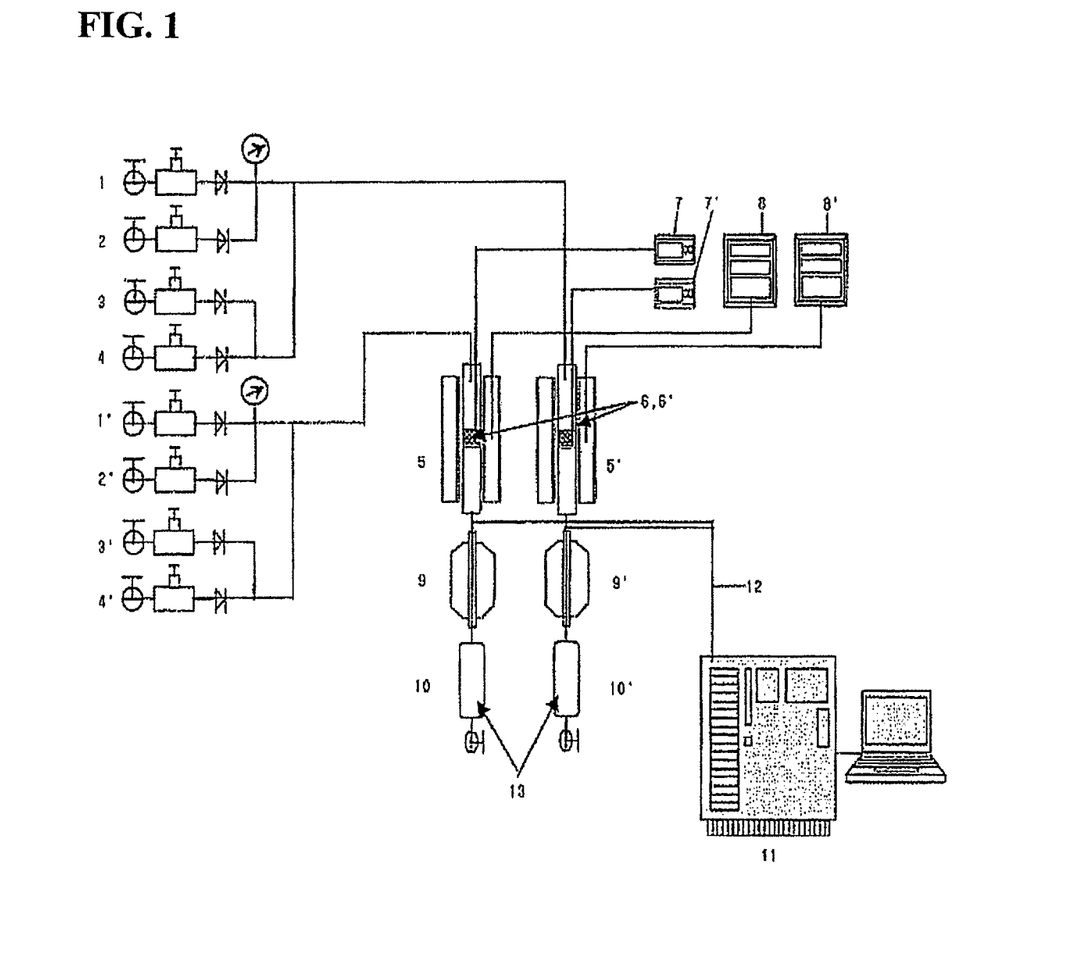
FIG. 1 schematically shows a system for measuring the reaction activity of a catalyst during the production of light olefins according to Examples of the present invention and Comparative Examples.

As shown in FIG. 1, a system for measuring the activity of the catalyst during the production of light olefins comprises a naphtha feed device 4, a water feed device 3, fixed-bed reactors 5 and 5', and an activity evaluation device, which are integrally connected with each other. In this case, naphtha specified in Table 1 above was used as feedstock. Naphtha and water fed by a liquid injection pump were mixed with each other in a preheater (not shown) at 300° C., and mixed with 6 ml/min of He and 3 ml/min of $N_2$ fed by helium feed devices 2 and 2' and nitrogen feed devices 1 and 1', respectively, and the mixture was fed into the fixed-bed reactors 5 and 5'. At this time, the amount and rate of each gas were controlled with a flow controller (not shown). The fixed-bed reactors are divided into an inner reactor and an outer reactor, in which the outer reactor, an Inconel reactor, was manufactured to a size of 38 cm in length and 4.6 cm in outer diameter, and the inner reactor made of stainless steel was manufactured to a size of 20 cm in length and 0.5 inches in outer diameter. The temperature within the reactors was indicated by temperature output devices 7 and 7', and reaction conditions were controlled by PID controllers (8 and 8' NP200; Han Young Electronics Co., Ltd, Korea).

The gas fed into the reactors was passed through the inner reactor and then passed through the outer reactor, through which 40 ml/min of He flowed. The bottom of the inner reactor was filled with the catalyst. The mixed gas was catalytically cracked through the catalyst layers 6 and 6', and after the reaction, vapor phase product 12 was quantified online by gas chromatography 11 (Model: HP 6890N). The remaining liquid phase product 13 passed through condensers 9 and 9' were recovered into storage tanks 10 and 10' and quantified by gas chromatography (Model: DS 6200; not shown). The amount of catalyst used in the catalytic cracking reaction was 0.5 g, the feed amount of each of naphtha and water was 0.5 g/h, and the reaction was carried out at 675° C.

The obtained results for conversion, selectivity to light olefins (ethylene and propylene) in the reaction product, and the ethylene/propylene weight ratio, are shown in Table 3 below.

EXAMPLE 2

A) Preparation of Catalyst

To 100 mL of distilled water, 10 g of HZSM-5 (Zeolyst) with a Si/Al molar ratio of 25, and 0.26 g of concentrated phosphoric acid (85% $H_3PO_4$), were added and stirred for about 20 minutes. To the stirred solution, 0.08 g of $Mg(OH)_2$ was added, and the mixture was adjusted to a pH of 2-3 using an aqueous nitric acid solution, followed by stirring at about 45° C. for about 20 minutes. After stirring the mixture at about 50° C. until water completely evaporated, vacuum filtration was performed to separate the solid product. The separated solid product was calcined in air at a temperature of 500° C. for 5 hours, thus preparing a Mg—$H_2PO_4$—HZSM-5 catalyst.

B) Steaming Step for Evaluation of Hydrothermal Stability

Steaming was carried out in the same manner as in Example 1.

C) Production of Light Olefins

The production of light olefins was carried out in the same manner as in Example 1.

The obtained results for conversion, selectivity to light olefins (ethylene and propylene) in the reaction product, and the ethylene/propylene weight ratio are shown in Table 3 below.

EXAMPLE 3

A) Preparation of Catalyst

Slurry comprising 6.6 kg of the Mg—$H_2PO_4$—HZSM-5 prepared in the part (A) of Example 2, 0.7 kg of Y zeolite and 3 kg of an alumina binder was stirred, followed by spray drying, thus preparing a pelletized catalyst with an average particle size of 80 μm.

B) Steaming for Evaluation of Hydrothermal Stability

Steaming was carried out in the same manner as in Example 1.

C) Production of Light Olefins

In this Example, a fluidized-bed reaction system was used to measure the activity of the catalyst during the production of light olefins. The fluidized-bed reaction system comprises a riser reactor, a regenerator, a striper and a stabilizer. The riser reactor is 2.5 m in height and 1 cm in diameter, the regenerator is 1.5 m in height and 12 cm in diameter, the stripper is 2 m in height and 10 cm in diameter, and the stabilizer is 1.7 m in height and 15 cm in diameter.

As feedstock, naphtha specified in Table 1 above was used.

At the riser inlet, the feedstock, steam and the catalyst are fed and mixed with each other, such that the feedstock is fed in 133 g/hr at 400° C., the steam is fed in 45 g/hr at 400° C., and the catalyst is fed in 5320 g/hr at 725° C. During the passage of the mixture through the riser, a fluidized-bed catalytic cracking reaction occurs, and the riser outlet has a temperature of 675° C. The mixture passed through the riser is separated into the catalyst and a fraction in the stripper at 500° C. The separated catalyst is recycled to the regenerator, and the fraction flows into the stabilizer. The catalyst introduced into the regenerator is regenerated in contact with air at 725° C., and the regenerated catalyst is fed again into the riser. The fraction fed into the stabilizer is separated into a gas component and a liquid component at −10° C.

The analysis of the gas component and liquid component fractions produced by the reaction was performed in the same manner as in Example 1.

The obtained results for conversion, selectivity to light olefins (ethylene and propylene) in the reaction product, and the ethylene/propylene weight ratio, are shown in Table 3 below.

EXAMPLE 4

A) Preparation of Catalyst

To 100 mL of distilled water, 10 g of HZSM-5 (Zeolyst) with a Si/Al molar ratio of 25, and 0.18 g of concentrated phosphoric acid (85% $H_3PO_4$), were added and stirred for about 20 minutes. To the stirred solution, 0.146 g of $Mg(OH)_2$ was added, and the mixture was adjusted to a pH of 12-13 using ammonia water, followed by stirring at about 45° C. for about 20 minutes. After stirring the mixture at about 50° C. until the water completely evaporated, vacuum filtration was performed to separate the solid product. The separated solid product was calcined in air at a temperature of about 500° C. for 5 hours, thus preparing a Mg—$PO_4$—HZSM-5 catalyst.

B. Steaming for Evaluation of Hydrothermal Stability

Steaming was carried out in the same manner as in Example 1.

C) Production of Light Olefins

This was carried out in the same manner as in Example 1.

The obtained results for conversion, selectivity to light olefins (ethylene and propylene) in the reaction product, and the ethylene/propylene weight ratio are shown in Table 3 below.

EXAMPLES 5 TO 10

A) Preparation of Catalysts

Catalysts were prepared in the same manner as in Example 1 except that the composition of the raw material mixture was changed as shown in Table 2 below.

B) Steaming for Evaluation of Hydrothermal Stability

Steaming was carried out in the same manner as in Example 1.

C) Production of Light Olefins

This was carried out in the same manner as in Example 1.

The obtained results for conversion, selectivity to light olefins (ethylene and propylene) in the reaction product, and the ethylene/propylene weight ratio, are shown in Table 3 below.

COMPARATIVE EXAMPLE 1

A) Preparation of Catalyst

An HZSM-5 catalyst was prepared by calcining 10 g of HZSM-5 (Si/Al=25; Zeolyst) in air at a temperature of about 500° C. for 5 hours.

B) Steaming for Evaluation of Hydrothermal Stability

Steaming was not carried out.

C) Production of Light Olefins

This was carried out in the same manner as in Example 1.

The obtained results for conversion, selectivity to light olefins (ethylene and propylene) in the reaction product, and the ethylene/propylene weight ratio are shown in Table 3 below.

COMPARATIVE EXAMPLE 2

A) Preparation of Catalyst

An HZSM-5 catalyst was prepared by calcining 10 g of HZSM-5 (Si/Al=25; Zeolyst) in air at a temperature of about 500° C. for 5 hours.

B) Steaming for Evaluation of Hydrothermal Stability

Steaming was carried out in the same manner as in Example 1.

C) Production of Light Olefins

This was carried out in the same manner as in Example 1.

The obtained results for conversion, selectivity to light olefins (ethylene and propylene) in the reaction product, and the ethylene/propylene weight ratio are shown in Table 3 below.

COMPARATIVE EXAMPLE 3

A) Preparation of Catalyst

To 100 mL of distilled water, 10 g of HZSM-5 (Si/Al=25; Zeolyst) and 0.15 g of concentrated phosphoric acid (85% $H_3PO_4$) were added. The mixture was adjusted to a pH of 7-8 using ammonia water, and then stirred at about 50° C. until water completely evaporated. Then, vacuum filtration was performed to separate the solid product. The separated solid product was calcined in air at a temperature of about 500° C. for 5 hours, thus preparing an $HPO_4$—HZSM-5 catalyst.

B) Steaming for Evaluation of Hydrothermal Stability

Steaming was carried out in the same manner as in Example 1.

C) Production of Light Olefins this was carried out in the same manner as in Example 1.

The obtained results for conversion, selectivity to light olefins (ethylene and propylene) in the reaction product, and the ethylene/propylene weight ratio are shown in Table 3 below.

COMPARATIVE EXAMPLE 4

A) Preparation of Catalyst

To 100 mL of distilled water, 10 g of HZSM-5 (Si/Al=25; Zeolyst) and 1.4 g of La(NO$_3$)$_3$.xH$_2$O were added. The mixture was stirred at about 50° C. until the water completely evaporated. The remaining material was vacuum filtered to separate a solid product. The separated solid product was calcined in air at a temperature of 500° C. for 5 hours, thus preparing a La—HZSM-5 catalyst.

B) Steaming for Evaluation of Hydrothermal Stability

Steaming was carried out in the same manner as in Example 1.

C) Production of Light Olefins this was carried out in the same manner as in Example 1.

The obtained results for conversion, selectivity to light olefins (ethylene and propylene) in the reaction product, and the ethylene/propylene weight ratio, are shown in Table 3 below.

COMPARATIVE EXAMPLE 5

A) Preparation of Catalyst

To 100 mL of distilled water, 10 g of HZSM-5 (Si/Al=25; Zeolyst) and 0.74 g of concentrated phosphoric acid (85% H$_3$PO$_4$) were added and stirred for about 20 minutes. To the solution, 1.40 g of La(NO$_3$)$_3$.xH$_2$O was added, and the mixture was adjusted to a pH of 7-8, followed by stirring at a temperature of about 45° C. for 20 minutes. After stirring the mixture at about 50° C. until water completely evaporated, the remaining material was vacuum filtered to separate the solid product. The separated solid product was calcined in air at a temperature of about 500° C. for 5 hours, thus preparing a La—H$_3$PO$_4$—HZSM-5 catalyst.

B) Steaming for Evaluation of Hydrothermal Stability

Steaming was carried out in the same manner as in Example 1.

C) Production of Light Olefins

This was performed in the same manner as in Example 1.

The obtained results for conversion, selectivity to light olefins (ethylene and propylene) in the reaction product, and the ethylene/propylene weight ratio are shown in Table 3 below.

COMPARATIVE EXAMPLE 6

A) Preparation of Catalyst

To 100 mL of distilled water, 10 g of HZSM-5 (Si/Al=25; Zeolyst) and 0.55 g of concentrated phosphoric acid (85% H$_3$PO$_4$) were added, followed by stirring for 20 minutes. To the stirred solution, 1.58 g of Mg(NO$_3$)$_2$.6H$_2$O was added, and the mixture was adjusted to a pH of 7-8 using ammonia water, and then stirred at a temperature of about 45° C. for about 20 minutes. After stirring the mixture at about 50° C. until the water completely evaporated, vacuum filtration was used to separate the solid product. The separated solid product was calcined in air at a temperature of about 500° C. for 5 hours, thus preparing a Mg—H$_3$PO$_4$—HZSM-5 catalyst.

B) Steaming for Evaluation of Hydrothermal Stability

Steaming was carried out in the same manner as in Example 1.

C) Production of Light Olefins

This was carried out in the same manner as in Example 1.

The obtained results for conversion, selectivity to light olefins (ethylene and propylene) in the reaction product, and the ethylene/propylene weight ratio, are shown in Table 3 below.

COMPARATIVE EXAMPLE 7

A) Preparation of Catalyst

A catalyst was prepared according to a method disclosed in U.S. Pat. No. 6,211,104 B1. The catalyst was prepared in the following specific manner. To 40 g of a solution of 85% phosphoric acid and MgCl$_2$.6H$_2$O in distilled water, 20 g of NH$_4$-ZSM-5 was added and loaded with the metal ions, followed by stirring. Then, the loaded molecular sieve was dried in an oven at 120° C., and finally, calcined at 550° C. for 2 hour.

B) Steaming for Evaluation of Hydrothermal Stability

The catalyst was steamed in the same manner as in Example 1.

C) Production of Light Olefins

This was carried out in the same manner as in Example 1.

The obtained results for conversion, selectivity to light olefins (ethylene and propylene) in the reaction product, and the ethylene/propylene weight ratio are shown in Table 3 below.

TABLE 2

| | Zeolites | Alkaline earth metal salts | Transition/ heavy metal salts | Phosphate species |
|---|---|---|---|---|
| Example 1 | HZSM-5 | Mg(OH)$_2$ (1.5) | — | HPO$_4$ (1.5) |
| Example 2 | HZSM-5 | Mg(OH)$_2$ (1.5) | — | H$_2$PO$_4$ (1.5) |
| Example 3 | HZSM-5 | Mg(OH)$_2$ (1.5) | — | H$_2$PO$_4$ (1.5) |
| Example 4 | HZSM-5 | Mg(OH)$_2$ (1.5) | — | PO$_4$ (1.5) |
| Example 5 | HZSM-5 | MgCO$_3$ (1.5) | — | HPO$_4$ (1.5) |
| Example 6 | HZSM-5 | Ca(C$_2$O$_4$)(1.5) | — | HPO$_4$ (1.5) |
| Example 7 | HZSM-5 | — | Ce$_2$O$_3$ (2.0) | HPO$_4$ (1.5) |
| Example 8 | HZSM-5 | BaCO$_3$ (1.5) | — | H$_2$PO$_4$ (1.5) |
| Example 9 | HZSM-5 | — | La$_2$O$_3$ (1.7) | HPO$_4$ (1.7) |
| Example 10 | HZSM-11 | — | Fe(C$_2$O$_4$) (2.0) | HPO$_4$ (2.0) |
| Comparative Example 1 | HZSM-5 | — | — | — |

TABLE 2-continued

| | Composition (wt %) | | | |
|---|---|---|---|---|
| | Zeolites | Alkaline earth metal salts | Transition/ heavy metal salts | Phosphate species |
| Comparative Example 2 | HZSM-5 | — | — | — |
| Comparative Example 3 | HZSM-5 | — | — | $HPO_4$ (1.5) |
| Comparative Example 4 | HZSM-5 | — | $La(NO_3)_3 \cdot xH_2O$ (6.0) | — |
| Comparative Example 5 | HZSM-5 | — | $La(NO_3)_3 \cdot xH_2O$ (6.0) | $HPO_4$ (2.0) |
| Comparative Example 6 | HZSM-5 | $Mg(NO_3)_2 \cdot 6H_2O$ (1.5) | — | $HPO_4$ (1.5) |
| Comparative Example 7 | HZSM-5 | $MgCl_2 \cdot 6H_2O$ (3.0) | — | P (3.0) |

TABLE 3

| | Catalytic cracking reaction results (unit: wt %) | | | | |
|---|---|---|---|---|---|
| | Conversion (%) | $C2^=$ | $C3^=$ | $C2^= + C3^=$ | $C2^=/C3^=$ |
| Example 1 | 76.8 | 18.1 | 19.4 | 37.5 | 0.93 |
| Example 2 | 77.0 | 16.3 | 18.0 | 34.3 | 0.90 |
| Example 3 | 86.1 | 22.8 | 20.1 | 42.9 | 1.13 |
| Example 4 | 76.2 | 16.2 | 17.8 | 34.0 | 0.91 |
| Example 5 | 76.8 | 14.8 | 18.6 | 33.4 | 0.80 |
| Example 6 | 80.1 | 18.0 | 17.7 | 35.7 | 1.01 |
| Example 7 | 76.0 | 16.6 | 18.5 | 35.1 | 0.90 |
| Example 8 | 79.2 | 16.7 | 19.6 | 36.3 | 0.85 |
| Example 9 | 80.4 | 17.4 | 18.5 | 35.9 | 0.94 |
| Example 10 | 79.7 | 17.4 | 19.7 | 37.1 | 0.89 |
| Comparative Example 1 | 77.7 | 21.8 | 18.7 | 40.5 | 1.17 |
| Comparative Example 2 | 67.7 | 10.8 | 13.7 | 24.5 | 0.79 |
| Comparative Example 3 | 66.5 | 8.9 | 11.9 | 20.8 | 0.75 |
| Comparative Example 4 | 58.4 | 10.4 | 12.8 | 23.2 | 0.82 |
| Comparative Example 5 | 75.4 | 13.1 | 17.4 | 30.5 | 0.75 |
| Comparative Example 6 | 72.1 | 12.5 | 15.7 | 28.2 | 0.80 |
| Comparative Example 7 | | 13.6 | 16.3 | 29.9 | 0.83 |

As could be seen in Table 3, the reactivity of the catalyst had a difference between the light olefin production processes according to Examples and Comparative Examples. Namely, in the case of Examples 1-10 according to the present invention, even the use of the catalyst steamed in an atmosphere of high temperature and humidity (maintained at 750° C. in 100% steam for 24 hours) showed a high conversion of about 76-80 wt %, and at the same time, high selectivity corresponding to the sum of ethylene+propylene of about 33-37 wt % (ethylene/propylene weight ratio=about 0.8-1.0).

On the other hand, it could be observed that the unsteamed HZSM-5 used in Comparative Example 1 showed a conversion of 77.7 wt % and a sum of ethylene+propylene of 40.5 wt %, but the use of HZSM-5 steamed in a severe hydrothermal atmosphere as in Comparative Example 2 showed rapid reductions in conversion and the sum of ethylene+propylene to 67.7 wt % and 24.5 wt %, respectively. In Comparative Examples 2, 3, 4 and 6, the conversion was about 58-75 wt % and the sum of ethylene+propylene was 20-30 wt %, indicating that these Comparative Examples excluding Comparative Example 5 showed very low conversion and olefin production as compared to the inventive production process.

Meanwhile, Comparative Example 5 showed a conversion of about 75.4 wt % and a sum of ethylene+propylene of 30.5 wt %. These results can be seen to be inferior to those of Examples 1-9, and this is believed to be because the use of nitric acid salt, which is a water-soluble metal salt, not a water-insoluble salt, led to a reduction in hydrothermal stability.

Also, evaluated reactivity of the catalyst prepared according to the method described in U.S. Pat. No. 6,211,104 B1 was inferior to that of the inventive process.

As described above, in the inventive process, even the use of a catalyst that has been hydrothermally treated in an atmosphere of 100% steam at 750° C. for 24 hours, showed $C2^=+C3^==33-37\%$, whereas the use of HZSM-5, P—HZSM-5 and La—HZSM-5 catalysts showed $C2^=+C3^==23-24\%$, and the use of La—P—HZSM-5 showed $C2^=+C3^==$ about 30%. Also, adjusting the component and composition ratio of a chemical species of modifying the catalyst used in the olefin production process according to the present invention shows a characteristic in that the hydrothermal stability of the catalyst can be ensured and at the same time, the conversion and $C2^=/C3^=$ ratio in the olefin production process can be controlled. In addition, the inventive catalyst is excellent in reaction activity required in producing light olefins from naphtha containing $C_{2-12}$ hydrocarbons.

As described above, according to the present invention, the use of a certain catalyst having hydrothermal stability shows excellent reaction performance in selectively producing light olefins at high yield with high selectivity from hydrocarbon feedstock, particularly full-range naphtha, even in a severe process environment of high temperature and humidity. Particularly, the inventive process is highly useful in that it can maintain high cracking activity even at a temperature lower than reaction temperature required in the prior thermal cracking temperature for the production of light olefins, and thus, can produce light olefins with high selectivity and conversion from hydrocarbon feedstock.

Although the preferred embodiments of the present invention have been described for illustrative purposes, those skilled in the art will appreciate that simple modifications, additions, and substitutions are possible, without departing from the scope and spirit of the invention as disclosed in the accompanying claims.

What is claimed is:

1. A process for producing light olefins from hydrocarbon feedstock, comprising the steps of:

(a) providing full-range naphtha or kerosene as feedstock;

(b) feeding the feedstock into at least one fixed-bed or fluidized-bed reactor where it is allowed to react in the presence of a catalyst; and (c) separating and recovering light olefins from the effluent of the reaction zone; in which the catalyst consists of a product obtained by the water evaporation of a raw material mixture comprising 100 parts by weight of a molecular sieve with a framework of —Si—OH—Al— groups, 0.01-5.0 parts by weight of a water-insoluble metal salt with a solubility product (Ksp) of less than $10^{-4}$, and 0.05-17.0 parts by weight of a phosphate compound, wherein the water-insoluble metal salt is an oxide, hydroxide, or oxalate of at least one metal selected from a group consisting of alkaline earth metals, transition metals, and heavy metals having an oxidation state of $^{+}3$ to $^{+}5$.

2. The process of claim 1, wherein the feed stock is naphtha containing $C_{2-15}$ hydrocarbons.

3. The process of claim 1, wherein the total content of paraffin components (n-paraffin and iso-paraffin) in the feedstock is 60-90% by weight, and the content of olefins in the feedstock is less than 20% by weight.

4. The process of claim 2, which further comprising the steps of mixing $C_{4-5}$ hydrocarbons remaining after the separation and recovery of light olefins in the step (c) with naphtha and providing the $C_{4-5}$ hydrocarbon/naphtha mixture as feedstock.

5. The process of claim 1, wherein, if the reactor is a fluidized-bed reactor, the reaction is then carried out at a temperature of 500-750° C., a hydrocarbon/steam weight ratio of 0.01-10, a catalyst/hydrocarbon weight ratio of 1-50, and a hydrocarbon residence time of 0.1-600 seconds.

6. The process of claim 1, wherein, if the reactor is a fixed-bed reactor, the reaction is then carried out at a temperature of 500-750° C., a hydrocarbon/steam weight ratio of 0.01-10, and a space velocity of $0.1\text{-}20^{-1}$.

7. The process of claim 1, wherein, when the catalyst is steamed in an atmosphere of 100% steam at 750° C. for 24 hours, the total content of ethylene and propylene in the effluent of the reaction zone is more than 30% by weight, and the ethylene/propylene weight ratio is 0.25-1.5.

* * * * *